(12) United States Patent
Wong et al.

(10) Patent No.: US 6,506,742 B2
(45) Date of Patent: Jan. 14, 2003

(54) SOLUBLE CONTRACEPTIVE LIQUID FORMULATION

(75) Inventors: George Wong, Belle Mead, NJ (US); Shifeng Wei, Belle Mead, NJ (US); Herling Uang, Somerset, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/727,871

(22) Filed: Dec. 1, 2000

(65) Prior Publication Data

US 2002/0103179 A1 Aug. 1, 2002

Related U.S. Application Data

(60) Provisional application No. 60/170,301, filed on Dec. 13, 1999.

(51) Int. Cl.[7] ............................................... A61K 31/56
(52) U.S. Cl. ......................... 514/178; 514/182; 514/843
(58) Field of Search ................................. 514/182, 843, 514/178

(56) References Cited

FOREIGN PATENT DOCUMENTS

| CN | 92101531.3 | 9/1993 |
|----|-----------|--------|
| DE | 19539860  | 5/1996 |

OTHER PUBLICATIONS

Anongguo Yiyao Gongye Szzhi (Chinese Journal of Pharmaceuticals), vol. 23(3)(1992), pp. 108–110 Research on Solubilization of Paracetamol Solutions.

*Primary Examiner*—Elli Peselev

(57) ABSTRACT

This invention provides a convenient process for preparing an oral contraceptive liquid formulation having improved solubility, bioavailability and stability useful as a reference standard.

3 Claims, 2 Drawing Sheets

SOLUBLE CONTRACEPTIVE LIQUID FORMULATION

CROSS REFERENCE TO RELATED APPLICATIONS

This application claims the benefit under 35 U.S.C. §199(e) of prior application Ser. No. 60/170,301, filed Dec. 13, 1999.

FIELD OF THE INVENTION

This invention provides a process for preparing a pharmaceutically useful oral contraceptive liquid formulation. More particularly, this invention provides a convenient process for preparing a oral contraceptive liquid formulation using certain ingredients having improved solubility, bioavailability and stability and pharmaceutically useful as a reference standard for comparing the bioavailability of another oral contraceptive formulation.

BACKGROUND OF THE INVENTION

Pharmaceutical manufacturers are required to compare the bioavailability of dosage forms after formulation changes have been made. For example, the bioavailability of an approved formulation of a tablet batch produced at commercial scale is compared with that of a formulation for which approval is sought, hereinafter referred to as a "biobatch." A comparative bioavailability study must then be conducted wherein tablets from the approved and biobatch formulation are each administered to volunteers. Plasma samples are then drawn and the amount of active agent present is analyzed. For an agent that is metabolized quickly after absorption, though, relative bioavialability must be measured instead. The parent compound remains in such a low quantities for quickly metabolized agents that the plasma concentration cannot be measured due to analytical equipment limits of detection. Therefore, the amount of metabolite present serves as a measure of relative bioavailability.

Relative bioavailability of a biobatch formulation is determined by using a reference standard that delivers a known and measurable quantity of the active agent. Such a reference standard may be in the dosage form of an IV solution, an oral solution or a tablet. Many steroid contraceptive drugs, however, are either poorly soluble or completely insoluble in water. Therefore, formulating an IV reference standard for such drugs is subject to many problems associated with low aqueous solubility properties. While an IV reference standard will provide a higher dose of active agent, a suitable IV formulation is limited by the poor solubility of the active agent in water and is not as convenient to administer as a tablet.

Although a contraceptive reference standard in a tablet dosage form is convenient to administer, tablets can have the undesirable characteristic of slow dissolution and corresponding poor bioavailability. Moreover, tablet reference standards for low dose contraceptive formulations must also provide enough active agent to enable accurate measurement of the relative bioavailability for each formulation compared. Since a very small amount of active agent is present in such tablet formulations, an accurate quantitation of the agent in a low dose tablet used as a reference standard is accordingly very difficult to achieve.

While an oral solution as a reference standard is also convenient to administer, conventional excipients and processes for preparing an oral solution of contraceptive steroids result in both poor solubility and stability. Accordingly, there exists a need for a convenient process for preparing an orally administered contraceptive reference standard that overcomes the problems of poor solubility, bioavailability and stability associated with known methods of preparing such reference standards.

Norgestimate (NGM), ethinyl estradiol (EE) and 17-β estradiol ($E_2$) are contraceptive progestin and estrogen steroids known as active agents in oral contraceptive tablet combination formulations. NGM in combination with EE is marketed under the trademark Tricyclen® in a triphasic package containing tablets having 180, 215 and 250 μg NGM dosage strengths in combination with 35 μg EE. In addition, a monophasic package containing tablets having 250 μg NGM in combination with 35 μg EE is marketed under the trademark Cyclen®. Also, a hormone replacement therapy formulation approved for marketing under the trademark Prefest® contains tablets having 90 μg NGM in combination with 1 mg $E_2$. It is known that the poor solubility of NGM limits the rate of absorption. Also, after absorption, NGM is quickly metabolized to 17-deacetyl norgestimate (17-dNGM), wherein this metabolite is used as the measure of relative bioavailability. To accurately compare the bioavailabilities of contraceptive formulations, therefore, and in particular those described herein, the need remains for a convenient process for preparing an oral contraceptive liquid formulation that is soluble, bioavailable and stable and pharmaceutically useful as a reference standard.

Many attempts to increase the solubility of active drugs have been heretofore made by pharmaceutical manufacturers. For example, U.S. Pat. No. 5,681,822, herein incorporated by reference, discloses a 2-chloro-2'-deoxyadenosine intravenous formulation that was made more soluble and stable by the addition of selected solubilizing agents. This reference describes, however, a non-analogous formulation and process compared to the present invention. Further, WO 98/20340, discloses a process for determining the dissolution rate of tablet formulations of norgestimate in combination with ethinyl estradiol tablets. This reference also only describes an analytical procedure that is distinguished from that of the present invention. EP 0012523B2 discloses a dry solid form of a poorly soluble or water insoluble drug in a composition described as yielding a higher dissolution rate and increased bioavailability. This reference also describes a formulation and process that is unlike that of the present invention. State of the art technology and the indicated references have not, however, met the need for a conveniently prepared oral contraceptive liquid formulation that is soluble, bioavailable and stable and pharmaceutically useful as a reference standard.

It is an object of the present invention to provide a convenient process for preparing an oral contraceptive liquid formulation. It is another object of this invention to provide a oral contraceptive liquid formulation having improved solubility, bioavailability and stability that is pharmaceutically useful as a liquid reference standard.

SUMMARY OF THE INVENTION

The present invention provides a process for preparing an oral contraceptive liquid formulation that is surprisingly soluble, bioavailable and stable for use in bioavailability studies, thus overcoming the problems associated with poorly soluble or water insoluble contraceptive drugs. The process for preparing the present invention is convenient; in addition to weighing and measuring out the ingredients to be mixed, the entire process takes from 1 to 3 minutes to complete.

Accordingly, this invention provides a convenient process for preparing an oral contraceptive liquid formulation comprising:

(a) adding from about 15 µg to about 4.0 mg of a contraceptive to from about 1 mL to about 5 mL ethyl alcohol;

(b) adding to the solution of step (a) up to about 2 mL polyethylene glycol, wherein the average molecular weight of the polyethylene glycol is from about 200 to about 800, and;

(c) adding to the solution of step (b) up to about 3 mL water to afford the oral contraceptive liquid formulation.

In another embodiment of the invention, the instant formulation is a 5 mL dose of an oral contraceptive liquid formulation, wherein the dosage strength is from about 3 µg/mL to about 0.8 mg/mL.

DETAILED DESCRIPTION OF THE INVENTION

Figure 1:
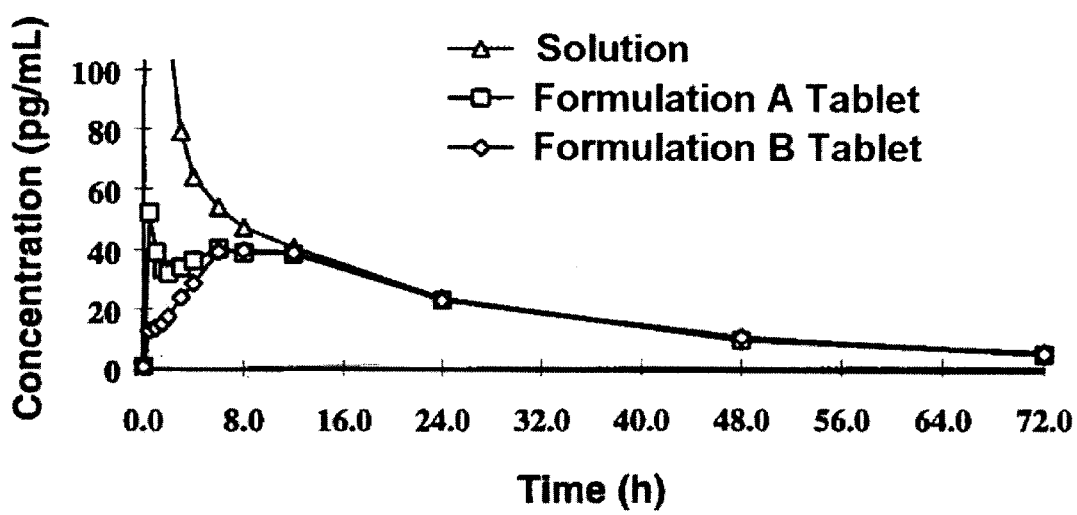
FIG. 1 shows the human plasma concentration over time of an $E_2$ contraceptive liquid formulation used as a reference standard to compare tablets from an approved Formulation A and biobatch Formulation B.

Ethyl alcohol (EtOH), polyethylene glycol (PEG) and water are known generally as agents for solubilizing pharmaceutical compounds. Relative to the above general description, the process of the present invention has preferred formulations wherein the above ingredients are present in certain volume ratios to provide optimum solubility, bioavailability and stability of the contraceptive liquid formulation.

In one embodiment of the invention, the PEG ingredient may have a molecular weight of from about 200 to about 800 and the EtOH has a concentration of about 95% USP. The water ingredient may be, without limitation, either purified water or water for injection. Preferably, an oral contraceptive liquid formulation contains the ingredients in concentrations as shown in Table 1.

TABLE 1

| Ingredient | % Volume | Volume | Active Ingredient |
|---|---|---|---|
| NGM | — | — | 15–500 µg |
| $E_2$ | — | — | 0.25–4.0 mg |
| EE | — | — | 15–100 µg |
| EtOH | 20–100% | 1–5 mL | |
| PEG 400 | 0–40% | 0–2 mL | |
| Water | 0–60% | 0–3 mL | |

Most preferably, the formulation of the present invention contains the ingredients and concentrations shown in Table 2.

TABLE 2

| Solvent | % Volume | Volume | Active Ingredient |
|---|---|---|---|
| NGM | — | — | 15–500 µg |
| $E_2$ | — | — | 0.25–4.0 mg |
| EE | — | — | 15–100 µg |
| EtOH | 25% | 1.25 mL | |
| PEG 400 | 25% | 1.25 mL | |
| Water | 50% | 2.5 mL | |

Where one of either EtOH, PEG 400 or water are contemplated within the preferred embodiment of the present invention, the other ingredients may be present in less than the amount prescribed in Table 2. Also, one or more of the contraceptive ingredients need not be present in the same formulation to achieve the results described herein. For example, the contraceptive ingredients may be premixed or added separately into a single liquid formulation or premixed individually in separate liquid formulations. Further, the various liquid formulations contemplated by the present invention may be administered separately or at about the same time.

To provide within the present invention for oral contraceptive liquid formulations that are pharmaceutically useful as reference standards, it may be necessary or desirable to include further compounds in the formulation. Such additional compounds are within the contemplated expertise of one of ordinary skill in the art and are included within the scope of the present invention.

GENERAL PREPARATION EXAMPLES

Oral contraceptive liquid formulations shown in Table 2 were prepared and found suitable for use as a liquid reference standard in accordance with the general preparation methods described below and illustrated more particularly in the specific preparation methods that follow. Since the following methods of preparing the instant formulation are illustrations, the scope of the present invention should not be construed as being limited by the methods expressed therein.

Example 1

Process for Preparing a 5 mL Oral Contraceptive Liquid Formulation Dose of a Combination of 250 µg NGM and 25 µg EE A formulation of the instant invention was prepared with water for injection to make a total volume of about 5.0 mL for oral administration as a reference standard. 25 mg NGM and 2.5 mg EE were added to about 125 mL ethyl alcohol and dissolved. To the resulting solution about 125 mL PEG 400 was added and mixed to achieve a clear solution. About 250 mL water was then added and mixed to obtain a clear solution of the oral contraceptive liquid formulation.

Example 2

Process for Preparing a 5 mL Oral Contraceptive Liquid Formulation Dose of a Combination of 180 µg NGM and 25 µg EE For a different dosing strength of the present invention, 18 mg NGM and 2.5 mg EE were used. The process for preparation of the oral contraceptive liquid formulation at this dose and dosage strength or any other dose and dosage strength or using any other mixtures of oral contraceptives is the same as in Example 1.

Example 3

Process for Preparing a Single 5 mL Oral Contraceptive Liquid Formulation Dose of a Combination of 250 μg NGM and 25 μg EE

A formulation of the instant invention is prepared with water for injection or purified water to make a total volume of about 5.0 mL for oral administration. 250 μg NGM and 25 μg EE are added to about 1.25 mL ethyl alcohol and dissolved. To the resulting solution about 1.25 mL PEG 400 is added and mixed to achieve a clear solution. About 2.5 mL water is then added and mixed to obtain a clear solution of the oral contraceptive liquid formulation.

Example 4

Stability Study of an Oral Contraceptive Liquid Formulation of a Combination of 250 μg NGM and 25 μg EE

A formulation as prepared in Examples 1 or 2, as shown in Table 3 were stored in a container at room temperature and tested periodically for the amount of contraceptive in solution. The reported figure of the contraceptives in solution is in percent of label claim.

TABLE 3

| Sample | Conc. (μg/5 mL) NGM | EE | Time | Storage Conditions | % Label NGM | EE |
|---|---|---|---|---|---|---|
| 1 | 250 | 25 | Initial | N/A | 101.6 | 100.9 |
| 2 | 250 | 25 | 24 hours | 25 C./60% RH | 98.6 | 102.3 |
| 3 | 250 | 25 | 3 months | 25 C./60% RH | 98.7 | 98.4 |
| 4 | 180 | 25 | Initial | N/A | 103.9 | 99.5 |
| 5 | 180 | 25 | 24 hours | 25 C./60% RH | 102.5 | 102 |
| 6 | 180 | 25 | 3 months | 25 C./60% RH | 101.4 | 97.4 |

The data indicated that the solubility and stability of NGM and EE in water is greatly increased by solubilizing the contraceptives according to the process of the present invention. Heretofore, no reference has disclosed a process whereby the solubility and stability of a single contraceptive or a combination of contraceptives in solution has been so markedly improved.

Example 5

Bioavailability Study Using an Oral Contraceptive Liquid Formulation of a Combination of 1 mg $E_2$ and 90 μg NGM as a Reference Standard

The bioequivalence of $E_2$ and its metabolites estrone ($E_1$) and Estrone Sulfate ($E_1S$) and of the NGM metabolites 17-deacetyl norgestimate (17d-NGM) and norgestrel (NG) from the $E_2$/NGM (1 mg/90 μg) Formulation A tablet and the Formulation B tablet of the same strength and the relative bioavailabilities of the tablet formulations compared to an equal dose of an oral contraceptive liquid formulation used as a reference standard were determined in an open-label, randomized, three-way crossover bioavailability study in 36 postmenopausal female subjects aged 44 to 65 years conducted for a total period of approximately 32 days. Equal numbers of subjects were randomly assigned to receive each of the three treatments (one per period) according to one of six possible treatment sequence groups. According to the study protocol on Study Day 1, subjects received a single oral dose of two $E_2$/NGM (1 mg/90 μg) Formulation A tablets or two $E_2$/NGM (1 mg/90 μg) Formulation B tablets or a single 5 mL oral dose of an $E_2$/NGM (2 mg/180 μg) liquid formulation used as a reference standard. The powder used to prepare the liquid formulation was sufficient to prepare about 500 mL of solution containing about 2.0 mg $E_2$ and about 180.0 μg NGM in each about 5.0 mL dose for oral administration. The treatments were crossed over on Study Days 15 and 29. Blood samples were drawn at set intervals after dosing to determine the plasma concentration of $E_2$, $E_1$, $E_1S$, 17d-NGM and NG.

The mean $E_2$ concentration results for the Formulation A tablet and the Formulation B tablet compared to each other and against the oral contraceptive liquid formulation used as a reference standard for all study treatments is summarized in Table 4 and illustrated in FIG. 1.

TABLE 4

| Parameter | Liquid Formulation | Formulation A | Formulation B |
|---|---|---|---|
| $C_{max}$ (pg/mL) | 522.3 (189.2) | 63.4 (45.2) | 43.7 (16.3) |
| AUC 0-* Ratio [a] | NA | 0.67 (0.16) | 0.65 (0.17) |

Figure 2:
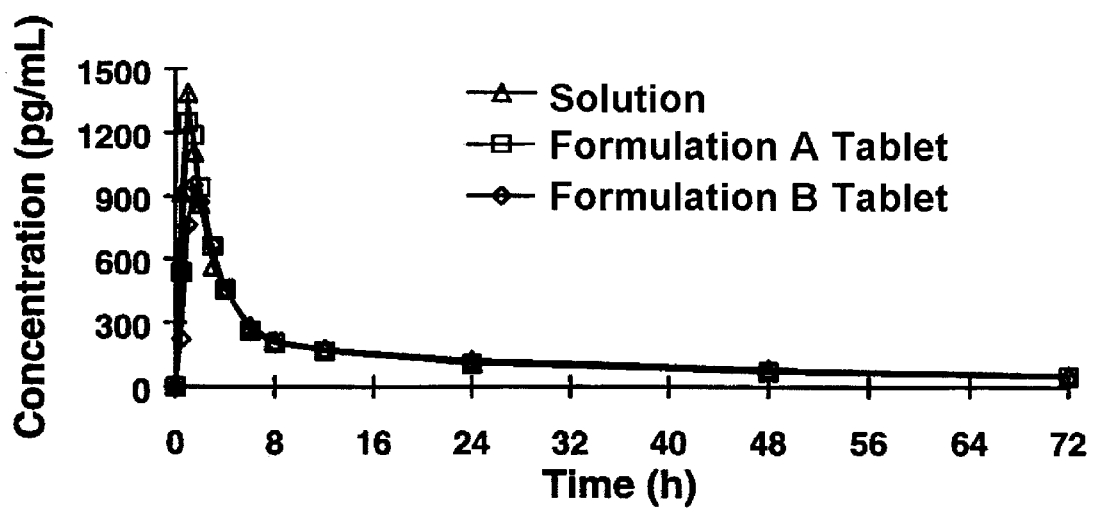
FIG. 2 shows the human plasma concentration of a 17-dNGM metabolite over time from a NGM contraceptive liquid formulation used as a reference standard to compare tablets from an approved Formulation A and biobatch Formulation B.

$C_{max}$ The peak plasma concentration
[a] Using the liquid formulation as a reference standard
AUC (0-*): Area Under the Curve for plasma concentration from time zero to the time of the last measurable concentration The mean 17d-NGM concentration results for the Formulation A tablet and the Formulation B tablet compared to each other and against the oral contraceptive liquid formulation used as a reference standard for all study treatments is summarized in Table 5 and illustrated in FIG. 2.

TABLE 5

| Parameter | Liquid Formulation | Formulation A | Formulation B |
|---|---|---|---|
| $C_{max}$ (pg/mL) | 1396.8 (338.8) | 1389.1 (290.8) | 1047.8 (326.9) |
| AUC 0-* Ratio [a] | NA | 0.93 (0.22) | 0.86 (0.22) |

$C_{max}$ The peak plasma concentration
[a] Using the liquid formulation as a reference standard
AUC (0-*): Area Under the Curve for plasma concentration from time zero to the time of the last measurable concentration The rate of absorption of $E_2$ was much faster from the liquid formulation used as a reference standard compared to the Formulation A tablet and the Formulation B tablet. The resulting $C_{max}$ and AUC values were approximately 10-fold higher than from the approved and biobatch tablet formulations. Similar results were obtained for 17-d NGM. The liquid formulation of a combination of 1 mg $E_2$ and 90 μg NGM, therefore, provided a reliable and consistent measure of relative bioavailability as a reference standard for a combination of oral contraceptive ingredients.

In addition to the foregoing, nonlimiting examples of practicing the process of the present invention, the oral contraceptive liquid formulation useful as a liquid reference standard of the invention may also be prepared for convenient oral administration using other means known to those of ordinary skill in the art which are intended to be included within the scope of the present invention.

What is claimed is:

1. A process for preparing an oral contraceptive liquid formulation consisting essentially of:

(a) forming a solution by adding from about 15 μg to about 4.0 mg of a contraceptive selected from the group consisting of norgestimate, 17-β estradiol, ethinyl estradiol and mixtures thereof to from about 1 mL to about 5 mL ethyl alcohol;

(b) adding to the solution of step (a) from about 1.25 mL up to about 2 mL polyethylene glycol, wherein the average molecular weight of the polyethylene glycol is from about 200 to about 800, and;

(c) adding to the solution of step (b) up to about 3 mL water to afford the oral contraceptive liquid formulation.

2. An oral contraceptive liquid formulation consisting essentially of:

(a) a contraceptive selected from the group consisting of norgestimate, 17-β estradiol ethinyl estradiol and mixtures thereof;

(b) from about 100 mL to about 500 mL ethyl alcohol;

(c) from about 125 mL up to about 200 mL polyethylene glycol 400; and (d) up to about 300 mL water.

3. An oral contraceptive liquid formulation consisting essentially of:

(a) a contraceptive selected from the group consisting of norgestimate, 17-β estradiol ethinyl estradiol and mixtures thereof;

(b) from about 1 mL to about 5 mL ethyl alcohol;

(c) from about 1.25 mL up to about 2 mL polyethylene glycol 400; and (d) up to about 3 mL water.

* * * * *